United States Patent [19]

Arnold et al.

[11] 4,018,855

[45] Apr. 19, 1977

[54] VULCANIZATION INHIBITING COMPOUNDS

[75] Inventors: Robert J. Arnold, Evanston; Marion J. Gattuso, Hoffman Estates, both of Ill.

[73] Assignee: UOP Inc., Des Plaines, Ill.

[22] Filed: Dec. 15, 1975

[21] Appl. No.: 641,121

Related U.S. Application Data

[63] Continuation-in-part of Ser. No. 533,573, Dec. 17, 1974, abandoned.

[52] U.S. Cl. .............................. 260/947; 260/814
[51] Int. Cl.² .......................................... C07F 9/24
[58] Field of Search ................................. 260/947

[56] References Cited

UNITED STATES PATENTS

| | | | |
|---|---|---|---|
| 2,957,020 | 10/1960 | Perkow | 260/959 X |
| 3,712,878 | 1/1973 | Nudenberg et al. | 260/927 R X |

FOREIGN PATENTS OR APPLICATIONS

| | | | |
|---|---|---|---|
| 1,022,587 | 6/1958 | Germany | 260/947 |

*Primary Examiner*—Richard L. Raymond
*Attorney, Agent, or Firm*—James R. Hoatson, Jr.; Raymond H. Nelson; William H. Page, II

[57] ABSTRACT

Novel compounds comprising substituted thiophosphoramides, as exemplified by N-cyclohexylthio-N-phenyldiethylphosphoramide, may be used to inhibit the premature vulcanization of vulcanizable rubber formulations.

6 Claims, No Drawings

VULCANIZATION INHIBITING COMPOUNDS

CROSS-REFERENCE TO RELATED APPLICATION

This application is a continuation-in-part of our co-pending application Ser. No. 533,573 filed Dec. 17, 1974, now abandoned, all teachings of which are incorporated herein by reference thereto.

BACKGROUND OF THE INVENTION

Rubber formulations, either synthetic or naturally occurring, must be processed in order to prepare finished products which are usable in industry. Among these processing features is the vulcanization of the rubber mixture by means well known in the art. In this respect various changes in the processing of rubber formulations have been adopted to facilitate the aforesaid processing, thereby improving the properties of the rubber products. When the rubber mixtures contain vulcanizing agents such as sulfur and accelerators, a certain amount of premature vulcanization, which is known in the trade as scorching, may occur prior to the proper vulcanization. In addition, other compounds may also be present in the rubber formulation which will also adversely effect the induction time or scorch duration period prior to vulcanization. For example, the rubber formulation may contain an antiozonant therein in order to impart protection to the finished rubber product against ozone cracking. Among the more popular antiozonants which are utilized for this purpose are the phenylenediamine type of compounds. However, this type of antiozonant appears to promote scorching or premature vulcanization. Another material which may be present and which may have an adverse effect on the vulcanization period is a high pH furnace black which appears to lack the inherent inhibiting effect of the acidic channel blacks. In the past, it has been a common practice to utilize certain compounds to reduce the risk of scorching prior to vulcanization. However, such compounds have been of limited success and ofttimes have caused undesirable properties in the finished products.

In contrast to this, it has now been found that novel compounds comprising additional thiophosphoramides in which two of the substituents on the nitrogen atom comprise aryl, cycloalkyl, thioaryl, or thiocycloalkyl radicals may be utilized as vulcanization inhibitors in rubber formulations to allow control of premature scorch yet will afford products which do not exhibit the unwanted characteristics of rubber formulations containing other vulcanization inhibitors which have been used in the past. With respect to the novel substituted thiophosphoramides, the prior art has disclosed compounds which are similar in nature, yet do not possess the configuration of the novel compounds of the present invention. For example, German Patent No. 1,022,587 discloses substituted thiophosphoramides in which all of the substituents on the phosphorus atom contain alkyl radicals, there being two alkoxy radicals attached to the phosphorus atom and only one disubstituted nitrogen atom. However, this patent does not teach nor suggest the novel compounds of the type hereinafter set forth in greater detail, nor does the patent disclose that these compounds may be utilized as inhibitors against the premature vulcanization of rubber formulations. While other prior art references such as U.S. Pat. No. 2,957,020 have disclosed the equivalency of aryl or cycloalkyl radicals with alkyl radicals, there is no teaching of equivalency of alkyl, cycloalkyl and aryl radicals for the particular purpose of producing compounds which are effective inhibitors against the premature vulcanization of rubber.

The novel compounds of the present invention are specifically limited to compounds in which an alkoxy group is attached to a phosphorus atom while aryl or cycloalkyl radicals are attached to both the nitrogen and sulfur atoms of the compound. As will hereinafter be shown in greater detail, these novel compounds possess a specific utility in their ability to act as inhibitors against the premature vulcanization of rubber formulations.

This invention relates to novel compounds comprising substituted thiophosphoramides, and particularly to the use of these compounds as scorch inhibitors in the accelerated sulfur vulcanization of rubber formulations. More specifically the invention is directed to novel compounds comprising substituted thiophosphoramides in which the radicals on the nitrogen and sulfur atoms of the compound comprise either aryl or cycloalkyl radicals.

It is therefore an object of this invention to provide novel compounds of the type hereinafter set forth in greater detail, these compounds being useful as scorch inhibitors.

In one aspect an embodiment of this invention resides in a compound having the generic formula:

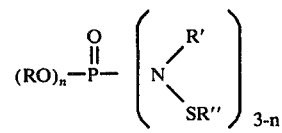

in which R is an alkyl radical of from 1 to 6 carbon atoms, R' and R'' are phenyl or cycloalkyl radicals containing from 4 to about 8 carbon atoms and $n$ is an integer of from 1 to 2.

A specific embodiment of this invention is found in a novel compound comprising N-cyclohexylthio-N-phenyldiethylphosphoramide.

Other objects and embodiments will be found in the following further detailed description of the present invention.

As hereinbefore set forth, the present invention is concerned with novel compounds for inhibiting the scorch in the accelerated sulfur vulcanization of rubber, the compounds in particular comprising the reaction product between a substituted phosphoramide and a sulfenyl chloride. The novel compounds of the present invention may be prepared by reacting a substituted sulfenyl chloride with a substituted phosphoramide, the substituted sulfenyl compound being present in a molar ratio equal to the number of nitrogen equivalents present on the specific phosphoramide, or in other words $(3-n)$ moles of sulfenyl halide per mole of phosphoramide. The reaction is preferably effected at subambient or depressed temperatures ranging from about −10° up to about 20° C., and preferably in a range of from about −5° to about 5° C. In addition, the reaction may also be effected in the presence of an acid scavenger and an organic solvent of the types hereinafter set forth in greater detail.

Examples of cycloalkyl- or aryl-substituted sulfenyl halides and preferably substituted sulfenyl chlorides which may be employed as one of the starting materials in the present process will include those compounds having the generic formula:

$$R - S - X$$

in which R is selected from the group consisting of cycloalkyl of from 4 to about 8 carbon atoms, or aryl such as phenyl and tolyl radicals, and X is a halogen atom, preferably chlorine. Some representative compounds which may be enumerated will include cyclobutanesulfenyl chloride, cyclopentanesulfenyl chloride, cyclohexanesulfenyl chloride, cycloheptanesulfenyl chloride, cyclooctanesulfenyl chloride, benzenesulfenyl chloride, o-toluenesulfenyl chloride, m-toluenesulfenyl chloride, p-toluenesulfenyl chloride, etc.

The aforementioned substituted sulfenyl halides are reacted with substituted phosphoramides containing a cycloalkyl or aryl radical on the nitrogen atom which will possess the generic formula:

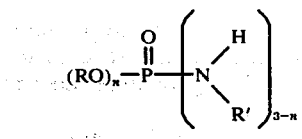

in which R consists of alkyl of from 1 to about 6 carbon atoms, R' is selected from the group consisting of cycloalkyl of from 4 to about 8 carbon atoms, and aryl radicals, and $n$ is an integer of from 1 to 2. Some representative examples of these compounds will include N-phenyldimethylphosphoramide, N-phenyldiethylphosphoramide, N-phenyldipropylphosphoramide, N-phenyldibutylphosphoramide, N-phenyldipentylphosphoramide, N-phenyldihexylphosphoramide, N-p-tolyldimethylphosphoramide, N-p-tolyldiethylphosphoramide, N-p-tolyldipropylphosphoramide, N-p-tolyldibutylphosphoramide, N-p-tolyldipentylphosphoramide, N-p-tolyldihexylphosphoramide, N-cyclobutyldimethylphosphoramide, N-cyclobutyldiethylphosphoramide, N-cyclohexyldipropylphosphoramide, N-cyclobutyldipentylphosphoramide, N-cyclopentyldimethylphosphoramide, N-cyclopentyldiethylphosphoramide, N-cyclopentyldihexylphosphoramide, N-cyclohexyldimethylphosphoramide, N-cyclohexyldiethylphosphoramide, N-cyclohexyldipropylphosphoramide, methyl-di(phenylamido)phosphate, ethyl-di(phenylamido)phosphate, propyl-di(phenylamido)phosphate, methyl-di(cyclohexylamido)phosphate, ethyl-di(cyclohexylamido)phosphate, propyl-di(cyclohexylamido)phosphate, butyl-di(cyclohexylamido)phosphate, hexyl-di(cyclohexylamido)phosphate, methyl-di(cycloheptylamido)phosphate, ethyl-di(cycloheptylamido)phosphate, propyl-di(cyclooctylamido)phosphate, amyl-di(cyclooctylamido)phosphate, etc. It is to be understood that the aforementioned substituted sulfenyl halides and substituted phosphoramides are only representative of the class of compounds which may be reacted to form the novel compounds of the present invention, and that said invention is not necessarily limited thereto.

As hereinbefore set forth, the reaction between the cycloalkyl- or aryl-substituted sulfenyl halide and the substituted phosphoramide in a molar ratio hereinbefore set forth is effected in the presence of an acid scavenger. In the preferred embodiment of this invention these acid scavengers will be basic in nature and will include such compounds as tertiary amines, examples of the tertiary amines which may be employed include trimethyl amine, triethyl amine, tri-n-propyl amine, triisopropyl amine, tri-n-butyl amine, tri-t-butyl amine, triphenyl amine. In addition, if so desired, the reaction may also be effected in the presence of an organic solvent such as dimethylformamide, diethylformamide, dipropylformamide, benzene, toluene, the xylenes, etc.

The preparation of the novel compounds of the present invention may be effected in any suitable manner and may comprise either a batch or continuous type operation. For example, when a batch type operation is used, a quantity of the substituted phosphoramide is placed in an appropriate apparatus along with the required acid scavenger and thereafore cooled, preferably from about 0° to about 10° C. utilizing any cooling means known in the art such as, for example, an ice bath. Following this, the substituted sulfenyl chloride, which may be prepared by treating a substituted disulfide with chlorine gas, is slowly added to the aforementioned substituted phosphoramide while maintaining the reaction mixture at depressed temperatures, said addition being accompanied by a vigorous mixing of the solution. Upon completion of the addition of the substituted sulfenyl chloride, the solution is allowed to warm to room temperature. After reaching room temperature, the solution is thereafter treated in a conventional manner such as washing, drying, separation, crystallization, recrystallization, etc., whereby the desired product is separated and recovered.

It is also contemplated within the scope of this invention that the desired product may be obtained in a continuous manner of operation. When this type of operation is employed, the starting materials are charged to a reaction zone which is maintained at the proper operation conditions of temperature and pressure. In addition, the reaction zone may contain the acid scavenger such as a tertiary amine and the solvent or, if so desired, these compounds may be admixed with one or both of the starting materials prior to entry into said reaction and the resulting mixture is charged thereto in a single stream. Upon completion of the desired reaction time, the effluent is continuously removed and subjected to separation and recovery means similar in nature to those hereinbefore set forth whereby the desired product is recovered while any unreacted starting materials may, after further treatment, be recycled to the reaction zone to form a portion of the feed stock.

The novel compounds of the present invention which may be prepared according to the above set forth process will possess the generic formula:

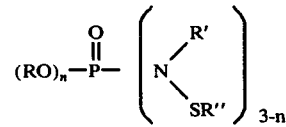

in which R is an alkyl radical of from 1 to 6 carbon atoms, R' and R" are phenyl or cycloalkyl radicals containing from 4 to about 8 carbon atoms and $n$ is an integer of from 1 to 2. Some specific examples of these compounds will include N-cyclobutylthio-N-phenyldimethylphosphoramide, N-cyclopentylthio-N-phenyldimethylphosphoramide, N-cyclohexylthio-N-phenyldimethylphosphoramide, N-cyclobutylthio-N-phenyldiethylphosphoramide, N-cyclopentylthio-N-phenyldiethylphosphoramide, N-cyclohexylthio-N-phenyldiethylphosphoramide, N-cyclopropylthio-N-phenyldibutylphosphoramide, N-cyclobutylthio-N-phenyldibutylphosphoramide, N-cyclopentylthio-N-phenyldibutylphosphoramide, N-cyclohexylthio-N-phenyldibutylphosphoramide, N-cyclopropylthio-N-phenyldihexylphosphoramide, N-cyclobutylthio-N-phenyldihexylphosphoramide, N-cyclopentylthio-N-phenyldihexylphosphoramide, N-cyclohexylthio-N-phenyldihexylphosphoramide, N-cycloheptylthio-N-phenyldibutylphosphoramide, N-phenylthio-N-phenyldimethylphosphoramide, N-phenylthio-N-phenyldiethylphosphoramide, N-phenylthio-N-phenyldipropylphosphoramide, N-phenylthio-N-phenyldibutylphosphoramide, N-cyclohexylthio-N-cyclohexyldimethylphosphoramide, N-cyclohexylthio-N-cyclohexyldiethylphosphoramide, N-cyclohexylthio-N-cyclohexyldipropylphosphoramide, N-cyclohexylthio-N-cyclohexyldibutylphosphoramide, N-cyclohexylthio-N-cyclohexyldihexylphosphoramide, N-cycloheptylthio-N-cycloheptyldimethylphosphoramide, N-cyclooctylthio-N-cyclooctyldiethylphosphoramide, methyl-di(N-phenylthiophenylamido)phosphate, ethyl-di(N-phenylthiophenylamido)phosphate, propyl-di(N-phenylthiophenylamido)phosphate, butyl-di(N-phenylthiophenylamido)phosphate, hexyl-di(N-phenylthiophenylamido)phosphate, methyl-di(N-phenylthiocyclohexylamido)phosphate, ethyl-di(N-phenylthiocyclohexylamido)phosphate, propyl-di(N-phenylthiocyclohexylamido)phosphate, butyl-di(N-phenylthiocyclohexylamido)phosphate, methyl-di(N-cyclohexylthiocyclohexylamido)phosphate, ethyl-di(N-cyclohexylthiocyclohexylamido)phosphate, propyl-di(N-cyclohexylthiocyclohexylamido)phosphate, butyl-di(N-cyclohexylthiocyclohexylamido)phosphate, hexyl-di(N-cyclohexylthiocyclohexylamido)phosphate, etc. It is to be understood that the aforementioned novel compounds are only representative of the class of compounds which may be prepared, and that the present invention is not necessarily limited thereto.

The aforementioned novel compounds comprising substituted thio-phosphoramides are used as inhibitors in rubber formulations in any suitable concentration, said concentration varying with the particular rubber formulation. In the preferred embodiment of the invention, the concentration may be within a range of from about 0.1 to about 5 and more specifically in a range of from about 0.1 to about 2 phr (parts per hundred parts by weight of rubber hydrocarbon).

As was previously set forth, these compounds are used in any vulcanizable rubber formulation, either synthetic or naturally occurring, in order to inhibit premature vulcanization. Some illustrative examples of the rubber formulations would include methyl rubber, Buna S, SBR (styrene-butadiene), polymers of butadiene or copolymers thereof with other monomers such as, for example, acrylonitrile, isobutylene, methyl methacrylate, cis-4-polybutadiene, butyl rubber, ethylene propylene terpolymers, etc.

As was hereinbefore discussed, in order to protect the finished rubber product against cracking due to ozone, an antiozonant generally is incorporated in the rubber formulation. Any suitable antiozonant may be used and, in one embodiment, is of the phenylenediamine type. This type of compound will include, for example, N,N'-di-sec-alkyl-p-phenylenediamines, in which each alkyl substituent contains from 3 to 12 carbon atoms, and N-phenyl-N'-sec-alkyl-p-phenylenediamines, in which the alkyl substituent contains from 3 to 12 carbon atoms, N,N'-dicyclohexyl-p-phenylenediamines, N-phenyl-N'-cyclohexyl-p-phenylenediamines, etc. In another embodiment, the rubber formulation may include antiozonants which are of the aminophenol types and include alkyl-substituted aminophenols in which the alkyl substituent on the nitrogen atom will contain from 3 to 20 carbon atoms or cycloalkyl-substituted p-aminophenols in which the cycloalkyl substituent on the nitrogen atom will contain from 3 to 12 carbon atoms in the ring. In most rubber formulations the antiozonant may be present in a concentration of from about 1 to about 5 parts by weight per hundred parts of rubber hydrocarbon in the formulation.

In addition to the antiozonant, the rubber formulation will generally include a vulcanization accelerator. Any suitable vulcanizing accelerator may be used including the conventional types such as 2-mercaptobenzothiazole, N-cyclohexyl-2-benzothiazole sulfenamide, N-tert-butyl-2-benzothiazole sulfenamide, 2-(morpholinothio)-benzothiazole, N-phenyl-2-benzothiazole sulfenamide, amine salts of mercaptobenzothiazole accelerators, etc. Other accelerators include tetramethylthiuram disulfide, thiocarbamyl sulfenamides, thioureas, xanthates, guanidine derivatives, etc. The vulcanizing accelerator will be used in conventional concentrations in the rubber formulation and may be within the range of from about 0.4 to about 3.0 parts by weight per hundred parts of rubber hydrocarbon in the formulation. It is understood that smaller or larger concentrations may be used when desired.

As hereinbefore set forth, the compounds of the present invention are also present in the rubber formulation in order to retard or inhibit the scorch in the accelerated sulfur vulcanization of the rubber formulation when said vulcanization is carried out at the usual temperature which may range from about 120° to about 170° C. or more. By utilizing these compounds, as will hereinafter be shown in greater detail in the appended examples, it is possible to retard the scorch which is present in the accelerated sulfur vulcanization of rubber thus preventing any premature vulcanization which is undesirable and which may lead to the preparation of finished rubber products which do not possess desirable characteristics.

The following examples are used to illustrate the novel compounds of the present invention and also to their use as prevulcanization inhibitors. However, these examples are not intended to limit the generally broad scope of the present invention in strict accordance therewith.

EXAMPLE I

To a solution containing 20.2 grams (0.2 mole) of triethyl amine, 27.6 grams (0.2 mole) of diethyl phosphite and 150 cc of carbon tetrachloride, was added dropwise with stirring, 20.0 grams (0.2 mole) of cyclohexyl amine which was dissolved in 50 cc of carbon tetrachloride. The reaction was exothermic in nature, heating the mixture to reflux temperature (about 75° C.). Upon completion of the addition to the diethyl phosphite solution, the mixture was stirred for an additional period of 3 hours while allowing the mixture to return to room temperature. Upon reaching room temperature, an equal volume of water was added to the resultant slurry, following which the organic layer was separated out, dried over magnesium sulfate and the carbon tetrachloride solvent was removed. Upon standing the brownish oil formed crystals which had a melting point of from 75.5° to 77.5° C., said crystals being N-cyclohexyldiethylphosphoramide.

Chlorine gas was condensed in a large test tube which was fitted with a condenser, the apparatus and chlorine being cooled to a dry ice temperature. Following this, 3.5 grams (0.05 mole) of chlorine was added as a gas on spontaneous evaporation to a stirred solution of 12.5 grams (0.05 mole) of cyclohexyl disulfide in 30 cc of methylene chloride, the solution being previously cooled to a temperature of from −5° to −10° C.

The cyclohexanesulfenyl chloride which was thus prepared is slowly added dropwise to a well-stirred, well-cooled solution of N-cyclohexyldiethylphosphoramide which was prepared according to the above paragraph while maintaining the temperature in a range of from −5° to 0° C. An exothermic reaction will occur with a concurrent precipitation of the hydrogen chloride salt of triethyl amine which is present in the dimethylformamide solution containing the N-cyclohexyldiethylphosphoramide. The slurry is stirred for a period of 1 hour while allowing the temperature of the solution to reach room temperature. Following this, water and pentane are added, the organic layer is washed several times with water, dried over magnesium sulfate and the solvent is removed. The desired product comprising N-cyclohexylthio-N-cyclohexyldiethylphosphoramide is recovered.

EXAMPLE II

In a manner similar to that set forth in Example I above, a solution of 50.5 grams (0.5 mole) of triethyl amine and 46.6 grams (0.5 mole) of aniline in 100 cc of carbon tetrachloride was added dropwise with stirring to a solution of 69.0 grams (0.5 mole) of diethyl phosphite in 250 cc of carbon tetrachloride. An exothermic reaction took place with the precipitation of the amine hydrochloride. Upon completion of the addition, the mixture was stirred for an additional period of 45 minutes and allowed to stand for a period of 16 hours. At the end of this time, an equal volume of water was added to the mixture, the organic layer was separated, washed with 200 cc of a 5% hydrochloric acid solution, followed by treatment with a saturated sodium bicarbonate solution, dried over magnesium sulfate and the carbon tetrachloride was removed under vacuum. This treatment resulted in an amber oil which crystallized upon standing. Recrystallization from boiling hexane afforded tan crystals having a melting point of from 93° to 94.5° C., said crystals being N-phenyldiethylphosphoramide.

In a manner similar to that set forth in Example I above, 3.5 grams (0.05 mole) of chlorine was added as a gas on spontaneous evaporation to a stirred solution of 12.5 grams (0.05 mole) of cyclohexyl disulfide in 30 cc of methylene chloride, the solution being previously cooled to a temperature of from −5° to −10° C.

A solution containing 22.9 grams (0.1 mole) of N-phenyldiethylphosphoramide, 11.1 grams (0.11 mole) of triethyl amine and 150 cc of dimethylformamide was cooled to a temperature of −5° C. To this solution was added 0.1 mole of cyclohexanesulfenyl chloride while stirring. A cloudy precipitate formed which remained while the resulting mixture was stirred for a period of 1 hour while warming to room temperature. At the end of this period, 200 cc of water and 100 cc of pentane were added, the organic layer was separated, dried over magnesium sulfate and the solvent was removed using a high vacuum at 50° C. An amber oil comprising N-cyclohexylthio-N-phenyldiethylphosphoramide was recovered.

EXAMPLE III

In this example 5.3 grams (0.075 mole) of chlorine was condensed in a large test tube and added subsurface as a gas on spontaneous evaporation to a well-stirred solution of 16.4 grams (0.075 mole) of phenyl disulfide which was dissolved in 50 cc of methylene chloride. The resulting solution containing 0.15 mole of benzenesulfenyl chloride was then added dropwise to a well-stirred solution of 34.4 grams (0.15 mole) of N-phenyldiethylphosphoramide which had been prepared in a manner similar to that set forth in Example II above and 16.7 grams (0.165 mole) of triethyl amine in 250 cc of benzene. After stirring the resulting mixture for an additional period of 30 minutes, the solid precipitate was removed by filtration. The filtrate was washed with water, dried over magnesium sulfate and evaporated to afford 49.6 grams of an amber oil, this amount representing a 98.2% yield.

EXAMPLE IV

In this example N-phenyldipropylphosphoramide is prepared by adding 0.5 mole of aniline dissolved in 100 cc of carbon tetrachloride to a solution of 0.5 mole of dipropyl phosphite dissolved in 250 cc of carbon tetrachloride, the addition being effected dropwise accompanied by continuous stirring. Upon completion of the addition, the mixture is stirred for an additional period of 3 hours while allowing the temperature of the reaction mixture which is at reflux to return to room temperature. The mixture is treated with an equal volume of water following which the organic layer is separated, washed with a 5% solution of hydrochloric acid, followed by washing with saturated sodium bicarbonate and dried over magnesium sulfate. The carbon tetrachloride is removed under vacuum and the resulting amber oil comprising N-phenyldipropylphosphoramide will crystallize upon standing.

The N-phenyldipropylphosphoramide which is prepared according to the above paragraph is treated with an equimolar portion of benzenesulfenyl chloride, the treatment being effected by adding the benzenesulfenyl chloride dropwise to a well-stirred, well-cooled solution of the N-phenyldipropylphosphoramide and triethyl amine in a dimethylformamide solvent. The mixture is stirred for a period of 1 hour while warming to room temperature from the 0° C. temperature at which the addition was effected. When the mixture has reached room temperature, water and pentane are added thereto, the organic layer is separated, dried over magnesium sulfate and the solvent removed at an elevated temperature. The desired product comprising N-phenylthio-N-phenyldipropylphosphoramide is recovered.

EXAMPLE V

In a manner similar to that set forth in the above example, ethyl-di(cyclohexylamido)phosphate is reacted with 2 moles of benzenesulfenyl chloride, the reaction being effected at a temperature in the range of from about −5° to about 0° C. in the presence of triethyl amine and a dimethylformamide solvent. The resulting mixture is allowed to warm to room temperature following which water and a pentane solvent are added, the organic layer is separated from the aqueous layer and dried over magnesium sulfate. The solvent is removed and the desired product comprising ethyl-di(N-phenylthiocyclohexylamido)phosphate is recovered.

EXAMPLE VI

To illustrate the ability of the novel compounds of the present invention to act as scorch inhibitors in accelerated vulcanization of rubber, the scorch properties of a rubber formulation were determined with a large rotor Mooney Viscometer at 250° F. (ASTM D-1077-55T). Values which represent the number of minutes for a rubber containing a curing agent to increase in viscosity by 1 and then by 10 points were obtained. This method simulates conditions encountered during milling and subsequent vulcanization. A long scorch time indicates a high resistance to scorching. A rubber formulation was prepared according to the following recipe:

| Ingredient | Parts By Weight |
|---|---|
| SBR 1502 | 100.00 |
| Furnace Black | 40.00 |
| Oil Extender | 10.00 |
| Zinc Oxide | 3.00 |
| Stearic Acid | 2.00 |
| Sulfur | 2.00 |
| Antiozonant | 2.00 |
| Accelerator* | 0.90 |
| Inhibitor | 0.50–1.00 |

*N-t-(butyl)benzothiazole-2-sulfenamide

The above ingredients were incorporated by conventional milling procedures.

In the following table the results of these tests are reported along with a control run in which no scorch inhibitor was used in the rubber formulation. In this table the blank test is reported as Run A. In Run B the rubber formulation contains 0.50 parts per hundred parts by weight of N-cyclohexylthio-N-phenyldiethylphosphoramide. Run C contains 1.0 parts of this compound. Run D contains 0.5 parts by weight of N-phenylthio-N-phenyldiethylphosphoramide and Run E contains 1.0 parts by weight of this compound.

| Run | Mooney Scorch Data | | | % Increase in 1 Pt Rise |
|---|---|---|---|---|
| | 1 Pt Rise (min) | 10 Pt Rise (min) | Δ10-1 (min) | |
| A | 5.6 | 6.8 | 1.2 | — |
| B | 6.9 | 8.4 | 1.5 | 23.2 |
| C | 11.1 | 12.8 | 1.8 | 98.0 |
| D | 7.9 | 9.1 | 1.2 | 41.0 |
| E | 8.8 | 10.0 | 1.2 | 57.1 |

It is to be noted from the above table that the rubber formulations which contain the novel compounds of the present invention acting as scorch inhibitors will exhibit a percentage increase in the 1 point rise time, the percentage increase ranging from 23.2% when using 0.5 parts by weight of N-cyclohexylthio-N-phenyldiethylphosphoramide to 98% when using 1.0 parts by weight of this compound, and in like manner, the percentage increase will range from 41.0% when using 0.5 parts by weight of N-phenylthio-N-phenyldiethylphosphoramide to 57.1% when using 1.0 parts by weight of this compound. This constitutes a clear indication of the fact that the novel compounds of the present invention possess the ability to inhibit the premature vulcanization of rubber formulations.

In like manner, when other compounds such as N-phenylthio-N-phenyldipropylphosphoramide, N-cyclohexylthio-N-cyclohexyldiethylphosphoramide, and ethyl-di(N-phenylthiocyclohexylamido)phosphate are admixed with similar rubber formulations, it will be found that the premature vulcanization of the rubber formulations will also be inhibited in like manner.

We claim as our invention:

1. A compound having the generic formula:

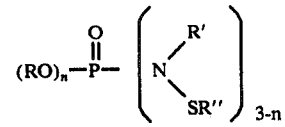

in which R is an alkyl radical of from 1 to 6 carbon atoms, R' and R" are phenyl or cycloalkyl radicals containing from 4 to about 8 carbon atoms and $n$ is an integer of from 1 to 2.

2. The compound of claim 1 being N-cyclohexylthio-N-phenyldiethylphosphoramide.

3. The compound of claim 1 being N-phenylthio-N-phenyldiethylphosphoramide.

4. The compound of claim 1 being N-phenylthio-N-phenyldipropylphosphoramide.

5. The compound of claim 1 being N-cyclohexylthio-N-cyclohexyldiethylphosphoramide.

6. The compound of claim 1 being ethyl-di(N-phenylthiocyclohexylamido)phosphate.

* * * * *